United States Patent
Lin et al.

(10) Patent No.: US 9,974,547 B2
(45) Date of Patent: May 22, 2018

(54) FEMORAL RESECTION GUIDE AND METHOD THEREOF

(71) Applicant: United Orthopedic Corporation, Hsinchu (TW)

(72) Inventors: Jason Lin, Hsinchu (TW); Ren-Hong Huang, Hsinchu (TW); Tzai-Chiu Yu, Hsinchu (TW)

(73) Assignee: UNITED ORTHOPEDIC CORPORATION, Hsinchu (TW)

( * ) Notice: Subject to any disclaimer, the term of this patent is extended or adjusted under 35 U.S.C. 154(b) by 610 days.

(21) Appl. No.: 14/592,502

(22) Filed: Jan. 8, 2015

(65) Prior Publication Data
US 2016/0089167 A1 Mar. 31, 2016

(30) Foreign Application Priority Data
Sep. 25, 2014 (TW) .............................. 103216989 U

(51) Int. Cl.
*A61B 17/15* (2006.01)
*A61B 90/00* (2016.01)

(52) U.S. Cl.
CPC ...... *A61B 17/155* (2013.01); *A61B 2090/067* (2016.02)

(58) Field of Classification Search
CPC .................................................. A61B 17/155
See application file for complete search history.

(56) References Cited

U.S. PATENT DOCUMENTS

| 5,486,178 A * | 1/1996 | Hodge | A61B 17/155 606/102 |
| 5,749,876 A * | 5/1998 | Duvillier | A61B 17/155 606/86 R |
| 5,776,137 A * | 7/1998 | Katz | A61B 17/155 606/102 |
| 6,013,081 A * | 1/2000 | Burkinshaw | A61B 17/155 606/102 |
| 7,488,324 B1 * | 2/2009 | Metzger | A61B 17/155 33/511 |

* cited by examiner

*Primary Examiner* — Zade Coley
*Assistant Examiner* — Olivia C Chang
(74) *Attorney, Agent, or Firm* — AEON Law, PLLC; Adam L.K. Phillipp; Manasi Vakil

(57) ABSTRACT

Disclosed is a femoral resection guide for measuring and guiding resection of anterior portion and posterior portion of a femur and method thereof. The femoral resection guide comprises a front block, a rear block, a reference gauge means and a locking means. A main scale marked portion is provided corresponding to the front scale member and the rear scale member in order to obtain a size of a patient's femur. The front block and the rear block are respectively provided with a resection guide surface for guiding a cutting tool to cut the femur. Moreover, the positions of the front resection guide surface and the rear resection guide surface in relation to the distal section of the femur can be adjusted, so that the problem of over or insufficient resection can be avoided, and the purchase cost and the storage space of the femoral resection instruments can be significantly reduced.

10 Claims, 20 Drawing Sheets

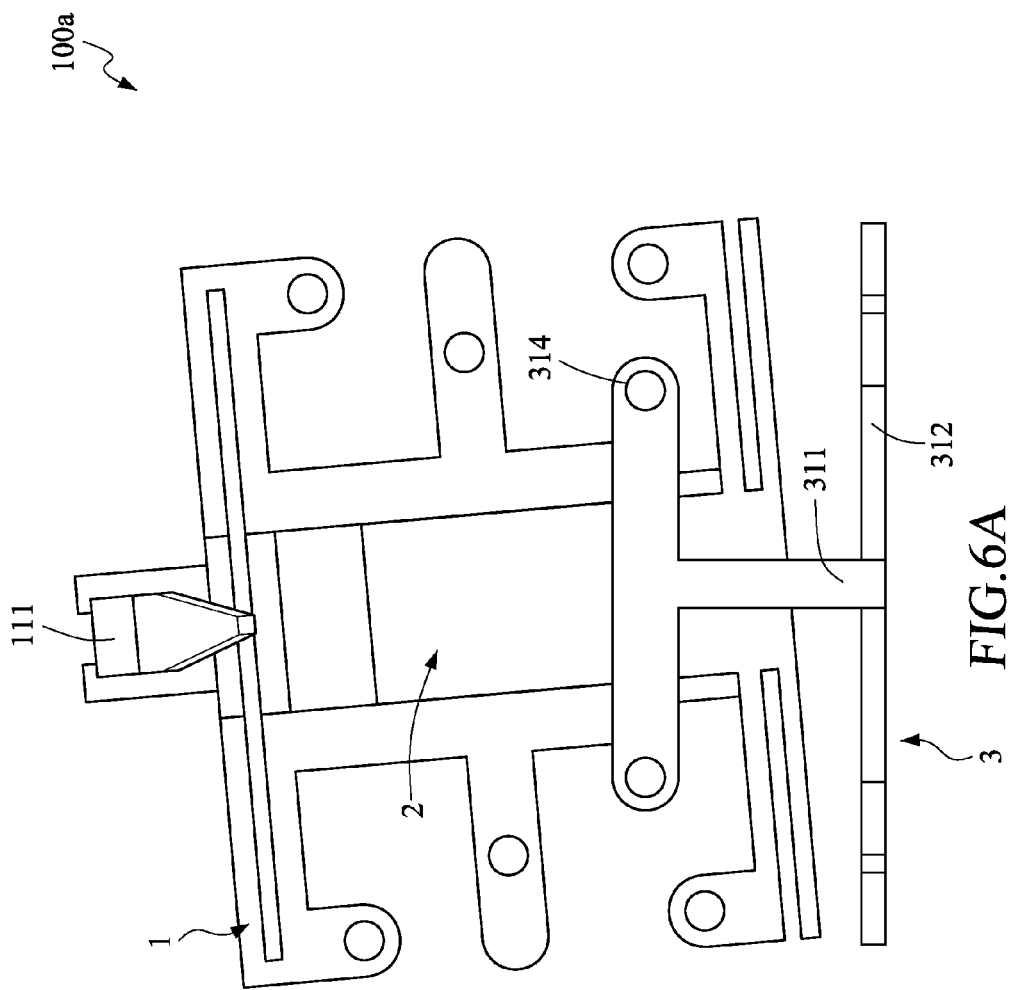

US 9,974,547 B2

FEMORAL RESECTION GUIDE AND METHOD THEREOF

CROSS-REFERENCE TO RELATED APPLICATION

This application claims priority to Taiwanese Patent Application No. 103216989, filed Sep. 25, 2014, which is hereby incorporated by reference.

FIELD OF THE INVENTION

The present invention relates to a femoral resection, and more particularly, to a femoral resection guide for measuring various sizes of femurs and for guiding resection of various sizes of femurs and a method thereof.

BACKGROUND OF THE INVENTION

In the femoral replacement surgery, a surgeon uses a measurement gauge to measure a size of a patient's femur so as to select an implant with suitable size and an implanting position according to the size obtained by the measurement gauge. Thereafter, a resection block corresponding to the size of implant is used to guide a cutting tool for the femoral resection.

The surgeon selects, according to the condition of patient's femur, one of the measurement gauge from different measurement gauges, each measurement gauge having different reference datum. One of the measurement gauge uses an anterior cortex as the reference datum to fix a front resection position of the femur, and thereafter a rear resection position of the femur is adjusted according to the size of the implant. Another one of the measurement gauge uses a posterior condyle as the reference datum to fix a rear resection position of the femur, and thereafter a front resection position of the femur is adjusted according to the size of the implant. However, when the patient's femur happens to be with size just between two implanting implants, the selection of either one of the measurement gauges will cause a problem that there will always be with over or insufficient resection of the anterior portion or the posterior portion to thus adversely affect the mobility of the patient's knee after the surgery.

In order to enhance the accuracy of the femoral resection, which can therefore achieve a perfect match between the implant and the patient's femur, the surgeon have to prepare different measurement gauges, each with different reference datum, and plural cutting blocks, each corresponding to every different size of implant. Therefore, the quantity of the femoral resection instruments becomes increased to cause a higher purchase cost and a larger storage space of the femoral resection instruments.

SUMMARY OF THE INVENTION

In view of the above, the present invention provides a femoral resection guide which can be used to adjustably position on the distal section of the femur to thus avoid the problem of having over or insufficient resection of the anterior portion or the posterior portion in such as way that the purchase cost and the storage space of the femoral resection instruments can be decreased.

The present invention utilizing a femoral resection guide for measuring and guiding resection of anterior portion and posterior portion of a femur, comprising:

a front block provided with a front datum member and a front scale member, wherein the front datum member is provided with a stylus for contacting an anterior cortex of the femur and has a front resection guide surface for guiding a cutting tool to resect the anterior portion of the femur, the front scale member is provided extending backwardly from the front datum member along a extending direction and is formed with a plurality of adjustably fixed portions arranged along the extending direction, and the front block has a front fixed hole by which the front block is enabled to fix on a distal section of the femur;

a rear block provided with a rear datum member and a rear scale member, wherein the rear datum member is provided with a rear resection guide surface for guiding a cutting tool to cut the posterior portion of the femur, the rear scale member is provided extending forwardly from the rear datum member along the extending direction and is slidingly engaged with the front scale member, and the rear block has a rear fixed hole by which the rear block is enabled to fix on the distal section of the femur;

a reference gauge means provided with a reference member, wherein the reference member is provided with a longitudinal portion extended along a length adjustment direction and a feet portion connected with the longitudinal portion, the longitudinal portion is provided on the rear block in an adjustment position along the length adjustment direction, the feet portion and the rear resection guide surface are provided therebetween with a spacing distance corresponding to a resection amount of the posterior portion of the femur, the feet portion is used to contact the posterior condyle of the femur; and a locking means provided between the front scale member and the rear scale member for locking them in a locked state or provided between the rear scale member and the reference gauge means for locking them in a locked state, wherein a main scale marked portion is provided corresponding to both the front scale member and the rear scale member, and a measurement is performed by sliding the rear scale member and the front scale member relative to each other along the extending direction to an adjusted position defined by a selected one of the adjustably fixed portions.

Another object of the present invention is to provide a femoral resection guide, wherein the front datum member is provided with a front guiding slot having the front resection guide surface.

Another object of the present invention is to provide a femoral resection guide, wherein the rear datum member is provided with a rear guiding slot having the rear resection guide surface.

Another object of the present invention is to provide a femoral resection guide, wherein a wing portion is formed extending from the front block or the rear block, and the wing portion has a positioning hole to allow a femoral cutting block to be installed.

Another object of the present invention is to provide a femoral resection guide, wherein the stylus is provided removable from the front datum member.

Another object of the present invention is to provide a femoral resection guide, wherein the rear scale member includes a connecting base in which the longitudinal portion is slidingly socketed.

Another object of the present invention is to provide a femoral resection guide, wherein a secondary scale marked portion is provided corresponding to the connecting base and the longitudinal portion to display the spacing distance between the feet portion and the rear resection guide surface.

Another object of the present invention is to provide a femoral resection guide, wherein a secondary scale marked portion is provided corresponding to the connecting base and the rear scale member to display the spacing distance between the feet portion and the rear resection guide surface.

Another object of the present invention is to provide a femoral resection guide, wherein the connecting base is pivotally disposed on the rear scale member in such a manner that the feet portion pivots on the connecting base, the reference gauge means includes a rotatable circular base and an eccentric rotor, the rotatable circular base is disposed on the rear scale member, the eccentric rotor is disposed on the rotatable circular base by being deviated from a rotation axis of the rotatable circular base, and the longitudinal portion is slidingly connected with the eccentric rotor.

Another object of the present invention is to provide a femoral resection guide, wherein an external rotation scale marked portion is provided corresponding to the rear block and the rotatable circular base to display the rotation angle of the feet portion.

Another object of the present invention is to provide a femoral resection guide, wherein the reference member has a fixed hole by which the reference member is allowed to fix on the distal section of the femur.

The present invention utilizing a method for using the femoral resection guide to cut femur at anterior portion and posterior portion, comprising steps of:

(a) obtaining the size of the femur by positioning the femoral resection guide on the distal section of the femur, and sliding the front block and the rear block relative to each other to lean the feet portion of the reference gauge means against a posterior condyle of the femur and make the stylus be in contact with the anterior cortex of the femur;

(b) adjusting a spacing distance between the front resection guide surface of the front block and the rear resection guide surface of the rear block, the spacing distance being corresponding to a size of an implant which is adapted to the femur;

(c) directing the front resection guide surface and the rear resection guide surface to a position corresponding to a portion to be cut on the distal section of the femur by adjusting the longitudinal portion of the reference gauge means in a direction along the length adjustment direction to a selected adjustably fixed portion and shifting the front block and the rear block relative to the reference gauge means;

(d) fixing the front block and the rear block on the distal section of the femur by passing a fixed nail through the fixed hole; and (e) cutting the portion to be cut of the femur by taking the front resection guide surface of the front block and/or the rear resection guide surface of the rear block as a reference resection plane.

Another object of the present invention is to provide a method, wherein the reference member of the reference gauge means is provided to rotate with respect to the rear block as the axis of rotation, and the method further includes, before the step (a), a step of rotating the front block and the rear block until to a rotation angle relative to the feet portion of the reference gauge means according to an external rotation angle of the femur.

Another object of the present invention is to provide a method, wherein in the step (b), the position of the rear resection guide surface of the rear block is adjusted by sliding the rear block relative to the front block.

Another object of the present invention is to provide a method, wherein in the step (b), the position of the front resection guide surface of the front block is adjusted by sliding the front block relative to the rear block and the feet portion.

Another object of the present invention is to provide a method, further comprising, before the step (b), a step of removing the stylus.

Another object of the present invention is to provide a method, further comprising, between the step (b) and the step (c), a step (b1) of fixing the front block on the distal section of the femur by passing a fixed nail through the fixed hole of the front block.

Another object of the present invention is to provide a method, further comprising, between the step (b1) and the step (c), a step (b2) of removing the fixed nail.

Another object of the present invention is to provide a method, further comprising, before the step (c), a step of fixing the reference gauge means on the distal section of the femur by passing a fixed nail through the fixed hole of the reference gauge means.

In view of the characteristic features as above, the femoral resection guide of the present invention can be used to measure the size of the femur and to guide the cutting tool for the resection of the anterior cortex and the posterior condyle of the femur by means of the resection guide surfaces, in such as way that the measurement gauge and the cutting block are being integrated. Further, in the present invention, the spacing distance between the front resection guide surface and the rear resection guide surface can be adjusted by sliding front block and the rear block in relation to each other, it does not need to purchase various cutting blocks that respectively corresponds to various sizes of implants. Therefore, the purchase cost and the storage space of the femoral resection instruments can be significantly reduced, and the operation of femoral resection guide becomes more convenient at the same time. In addition, the positions of the front resection guide surface and the rear resection guide surface in relation to the distal section of the femur can be adjusted according to the adjustment position, so that the problem of over or insufficient resection of the anterior cortex or the posterior condyle can be avoided by use of the femoral resection guide of the present invention when the size of the patient's femur happens to be between two most suitable implants. Accordingly, the mobility of the patient's knee is more improved after surgery.

BRIEF DESCRIPTION OF THE DRAWINGS

The structure and the technical means adopted by the present invention to achieve the above and other objectives can be best understood by referring to the following detailed description of the preferred embodiments and the accompanying drawings.

FIG. 6A is a back view of a femoral resection guide according to another embodiment of the present invention;

DETAILED DESCRIPTION OF THE PREFERRED EMBODIMENTS

Embodiments are described in detail below with reference to the FIGS. 1 to 18, and the description is used for explaining the embodiments of the present invention only, but is not intended to limit the described embodiments of the present invention.

Figure 3:
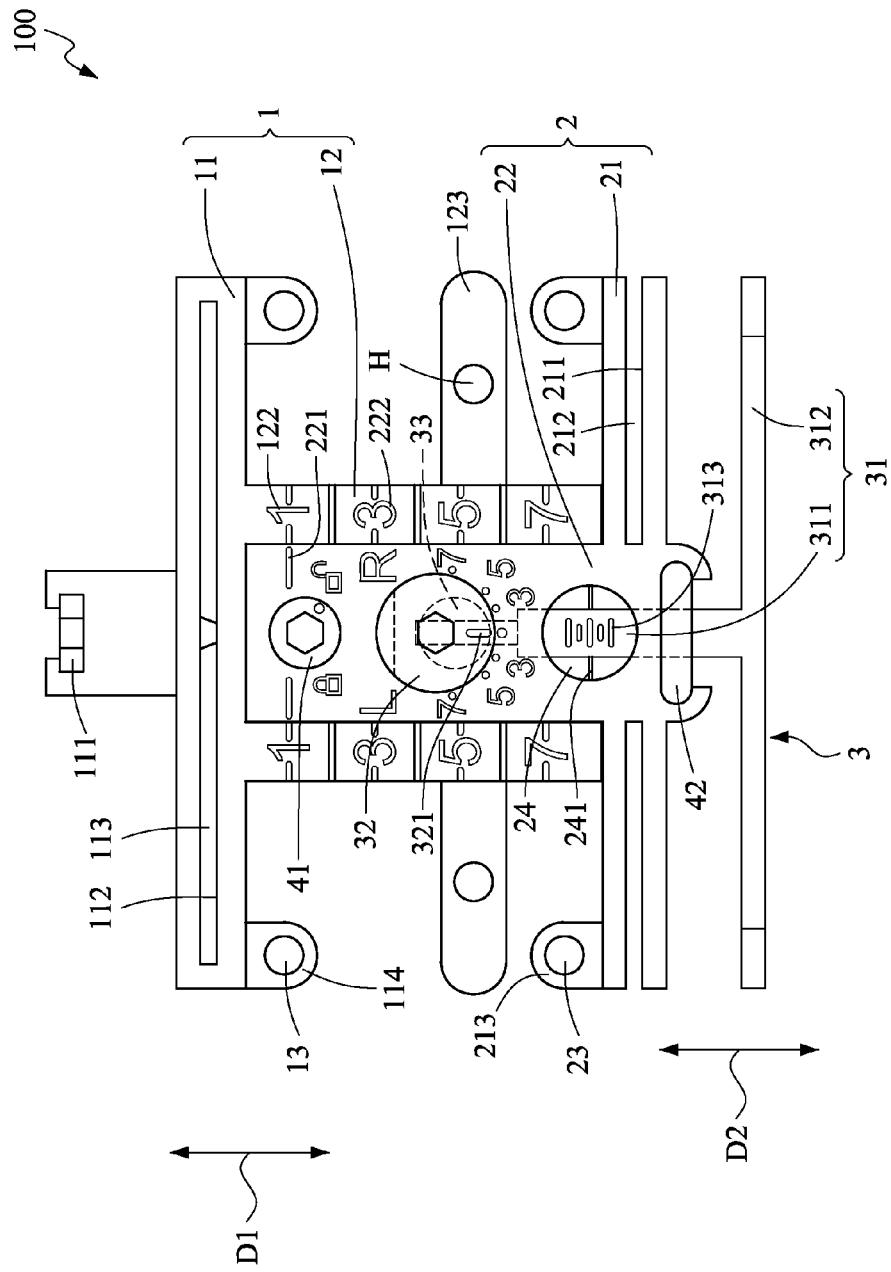
FIG. 3 is a schematic view illustrating the femoral resection guide when the rear block and a reference member are relatively sliding according to the embodiment of the present invention.
Figure 4:
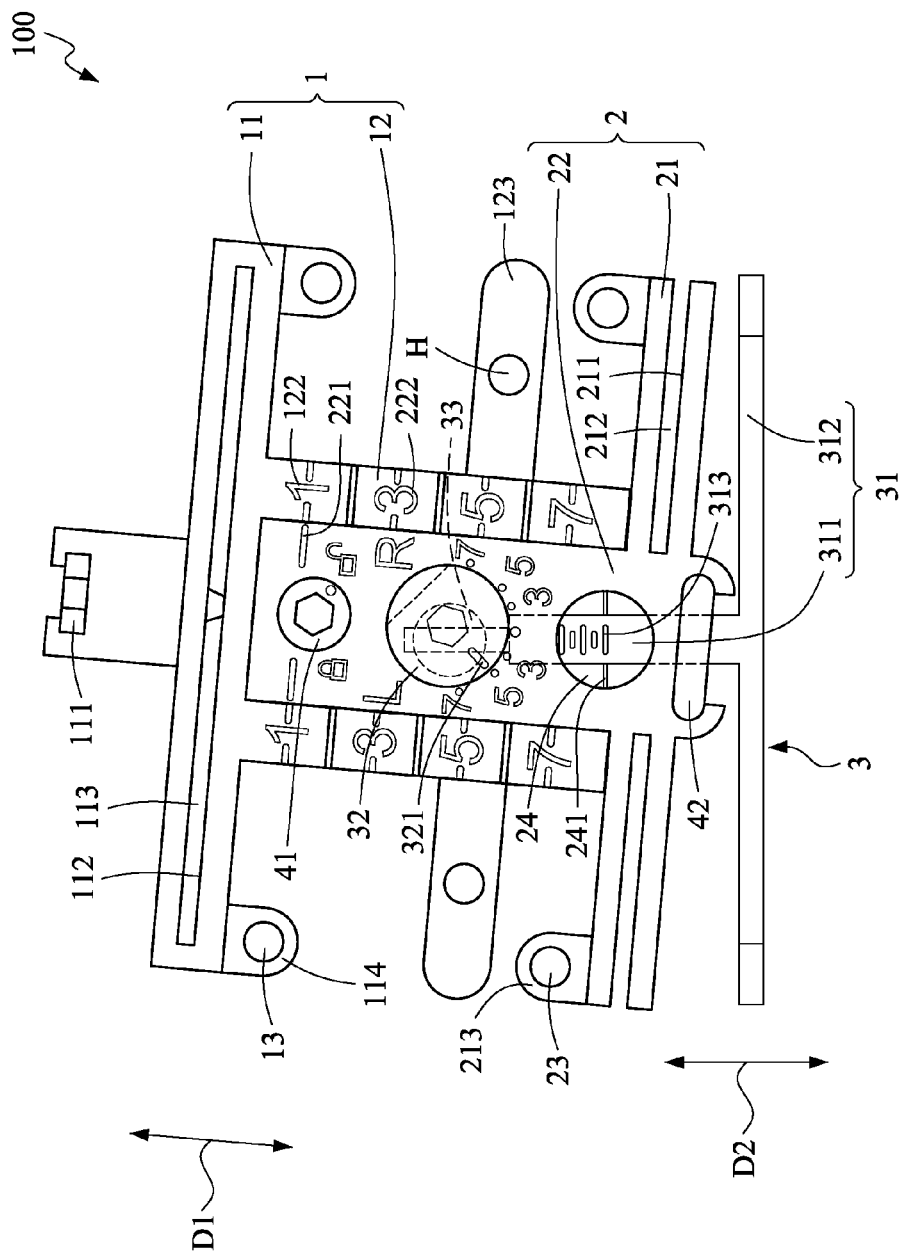
FIG. 4 is a schematic view illustrating the femoral resection guide when the rear block and a reference member are relatively rotating according to the embodiment of the present invention.
Figure 5:
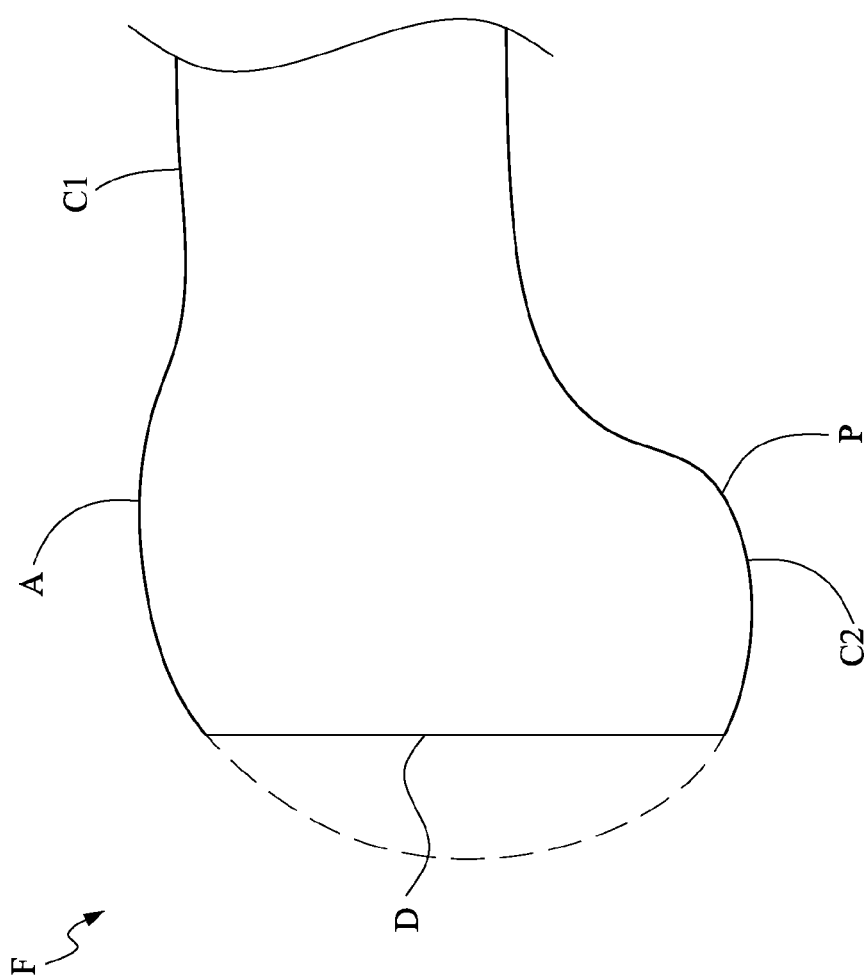
FIG. 5 is a schematic view of a femur of the present invention.

Referring to FIGS. 1 to 4, it is a femoral resection guide 100 for measuring and guiding resection of an anterior portion A and a posterior portion P of a femur F (as shown in FIG. 5) according to one embodiment of the present invention. The femoral resection guide 100 includes a front block 1, a rear block 2, a reference gauge means 3 and a locking means 4.

Figure 1:
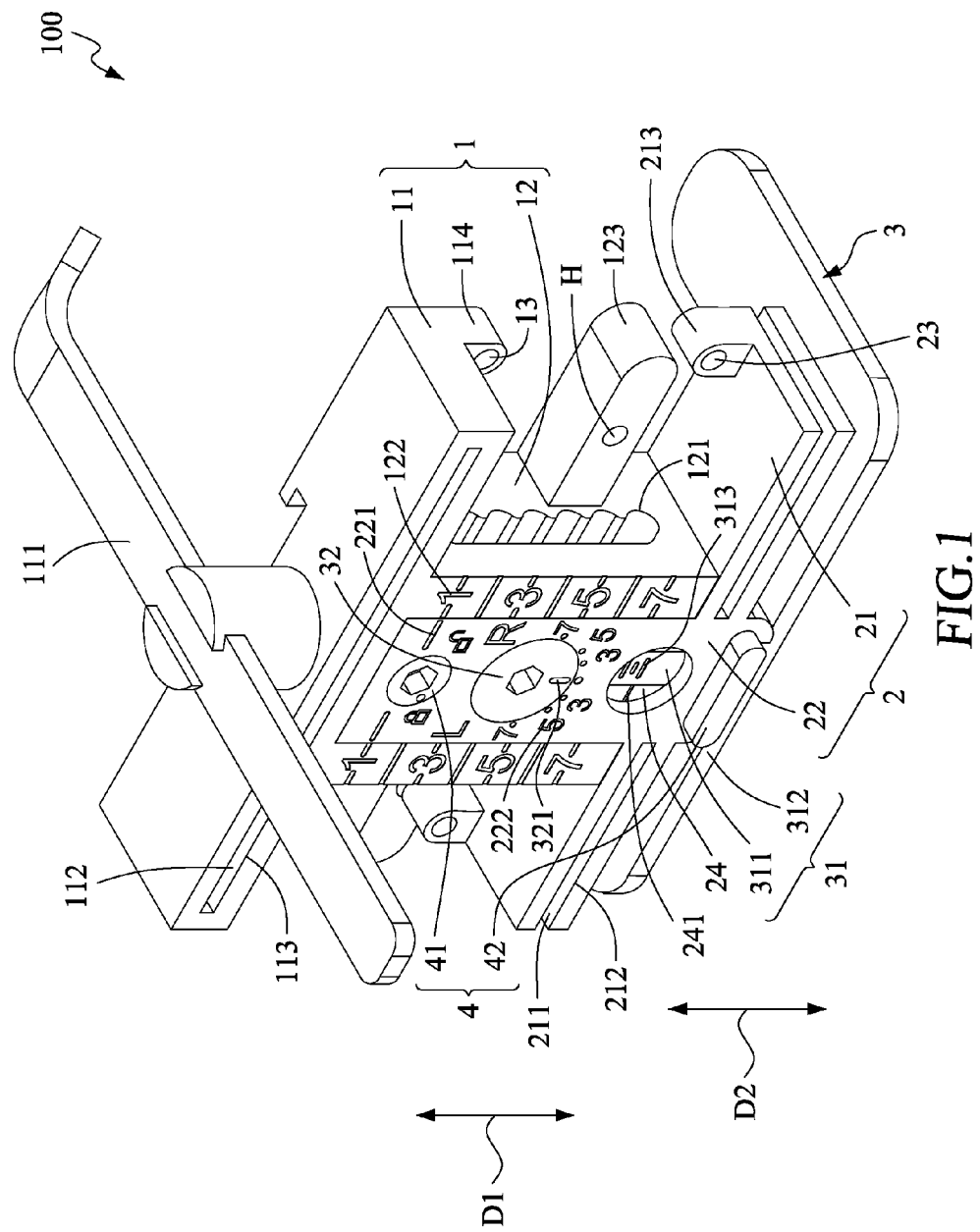
FIG. 1 is a stereogram illustrating a femoral resection guide according to an embodiment of the present invention.
Figure 2:
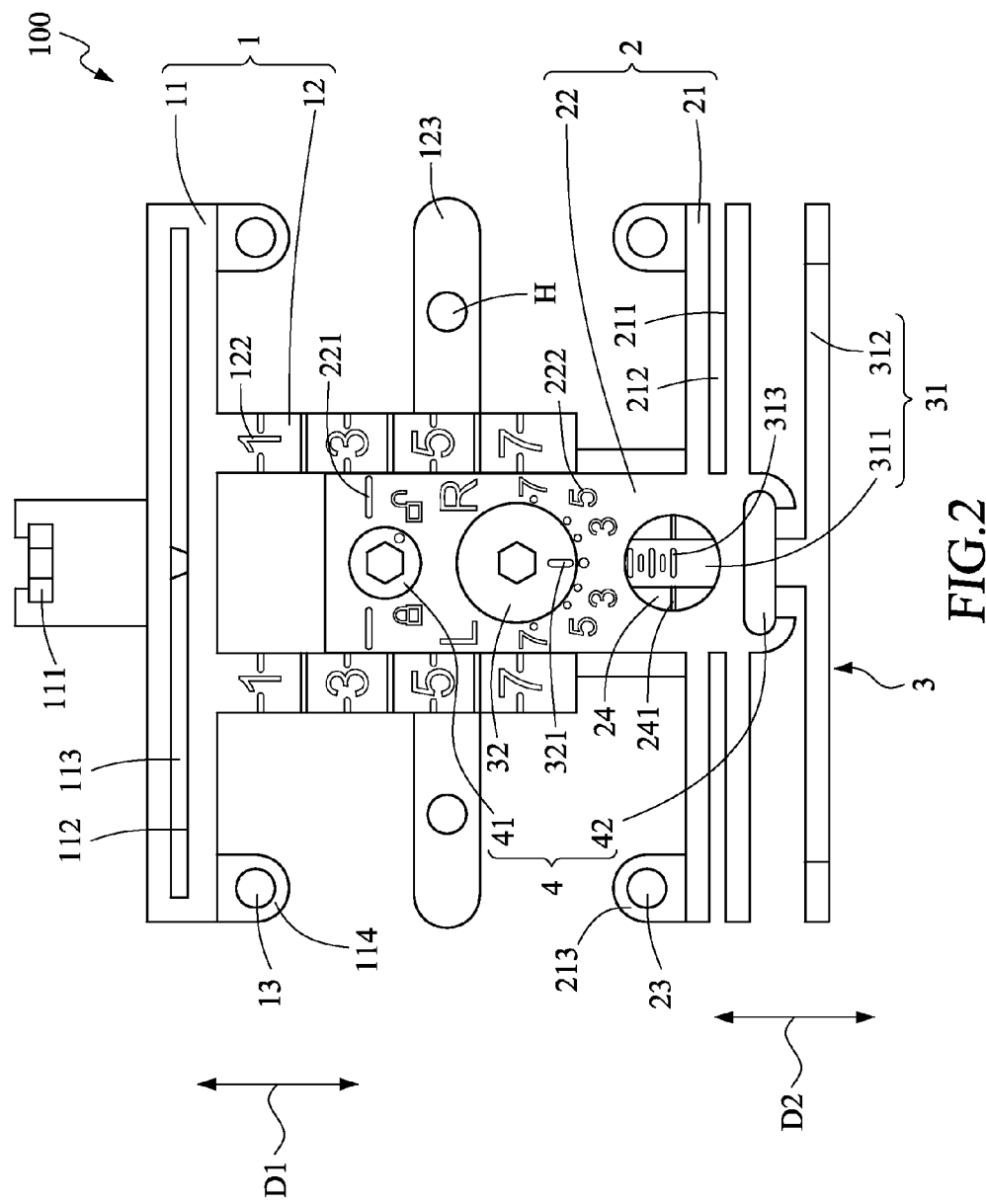
FIG. 2 is a schematic view illustrating the femoral resection guide when a front block and a rear block are relatively sliding according to the embodiment of the present invention.

Referring to FIGS. 1, 2 and 5, the front block 1 is provided with a front datum member 11 and two front scale members 12 parallel to each other. The front datum member 11 is provided with a stylus 111 for contacting the anterior cortex C1 of the femur F. Preferably, the stylus 111 is provided removable from the front datum member 11. The front datum member 11 has a front resection guide surface 112 for guiding a cutting tool (not shown) to resect the anterior portion A of the femur F. In this embodiment, the front datum member 11 is provided with a front guiding slot 113 having the front resection guide surface 112. However, the invention is not limited to this. The front resection guide surface 112 may be disposed on an upper surface of the front datum member 11.

Referring to FIGS. 1, 2 and 5, the front scale members 12 are provided extending backwardly from the front datum member 11 along an extending direction D1, and the front scale members 12 are formed with a plurality of adjustably fixed portions 121 arranged along the extending direction D1. The front block 1 has a front fixed hole 13 by which the front block 1 is enabled to be fixed on a distal section D of the femur F. Specifically, the front datum member 11 is formed with an extending portion 114 which is provided with the front fixed hole 13.

Referring to FIGS. 1, 2 and 5, the rear block 2 is provided with a rear datum member 21 and a rear scale member 22. The rear datum member 21 is provided with a rear resection guide surface 211 for guiding a cutting tool to cut the posterior portion P of the femur F. In this embodiment, the rear datum member 21 is provided with a rear guiding slot 212 having the rear resection guide surface 211. However, the invention is not limited to this. The rear resection guide surface 211 may be disposed on an upper surface of the rear datum member 21. The rear scale member 22 is provided extending forwardly from the rear datum member 21 along the extending direction D1, and the rear scale member 22 is slidden and engaged with the front scale members 12. Preferably, the rear block 2 has a rear fixed hole 23 and a connecting base 24. The rear fixed hole 23 is used to fix the rear block 2 on the distal section D of the femur F. Specifically, the rear datum member 21 is formed with an extending portion 213 which is provided with the rear fixed hole 23. Preferably, the connecting base 24 is pivotally disposed on the rear scale member 22.

Referring to FIGS. 1, 2 and 5, the front scale members 12 and the rear scale member 22 are provided with a main size-marking portion. The main size-marking portion includes a main size-indicating portion 122 provided on the front scale members 12 and a main size-reading portion 221 provided on the rear scale member 22. The main size-reading portion 221 is moved a related position of the main size-indicating portion 122 by sliding the front block 1 and the rear block 2 in relation to each other. It is noted that a spacing distance between the front resection guide surface 112 of the front block 1 and the rear resection guide surface 211 of the rear block 2 is read as a size of an implant when the main size-reading portion 221 marks on an integer index of the main size-indicating portion 122.

Referring to FIGS. 1 and 3, the reference gauge means 3 is provided with a reference member 31, a rotatable circular base 32 and an eccentric rotor 33. The reference member 31 is provided with a longitudinal portion 311 extending along a length adjustment direction D2 and a feet portion 312 connected with the longitudinal portion 311. The longitudinal portion 311 is slidden and socketed in the connecting base 24 of the rear scale member 22 in an adjustment position along the length adjustment direction D2. The connecting base 24 and the longitudinal portion 311 are integral to provide with a secondary scale marked portion to display the spacing distance between the feet portion 312 and the rear resection guide surface 211. Referring to FIGS. 1, 4 and 5, the feet portion 312 pivots on the connecting base 24 by the longitudinal portion 311. Referring to FIG. 6A, the reference member 31 is provided with a fixed hole 314 by which the reference member 31 is allowed to be fixed on the distal section D of the femur F. The rotatable circular base 32 is provided on the rear scale member 22. The eccentric rotor 33 is disposed in the rotatable circular base 32 by being deviated from a rotation axis of the rotatable circular base 32. The longitudinal portion 311 is slidden and connected with the eccentric rotor 33.

Figure 6B:
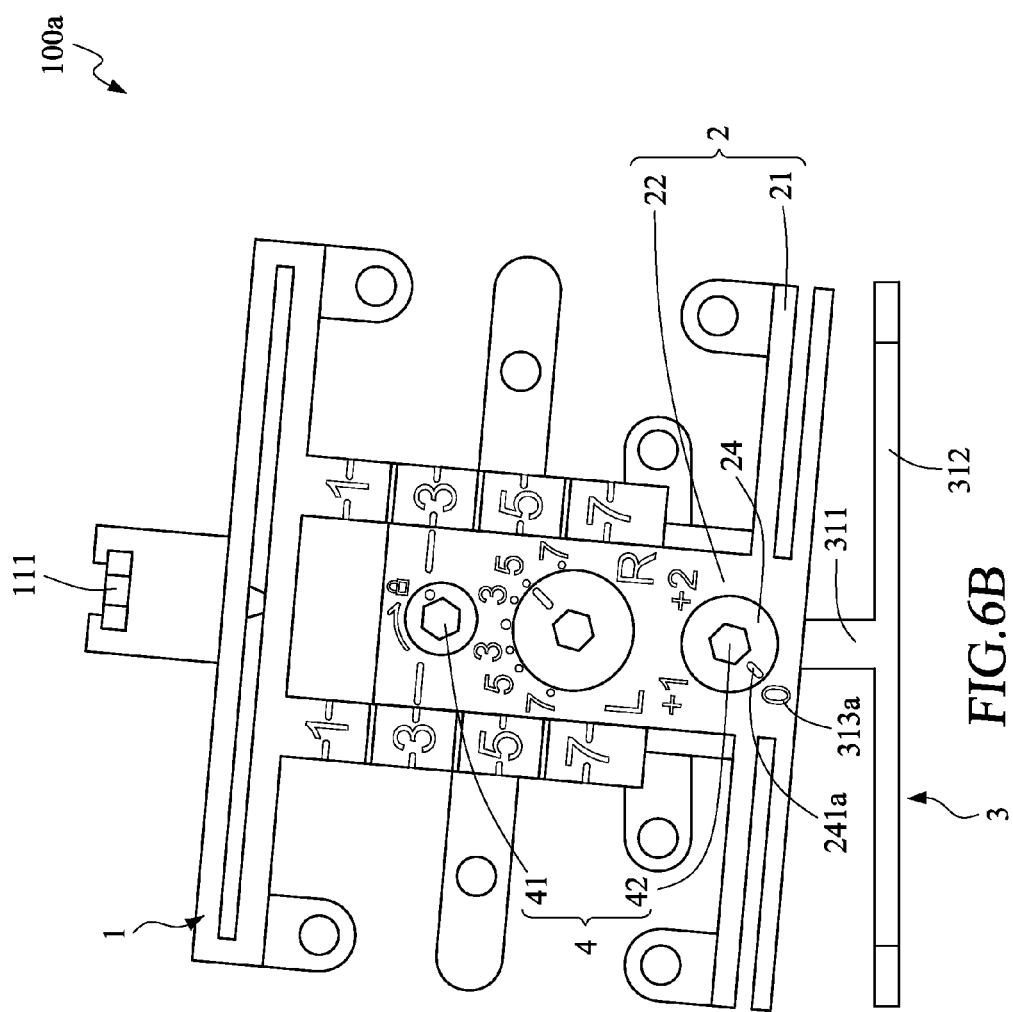
FIG. 6B is a front view of the femoral resection guide according to the another embodiment of the present invention.

Specifically, referring to FIG. 3, the secondary scale marked portion includes a secondary size-indicating portion 241 provided on the connecting base 24 and a secondary size-reading portion 313 provided on the longitudinal portion 311. The spacing distance between the feet portion 312 and the rear resection guide surface 211 is adjusted by sliding the reference gauge means 3 and the rear block 2 in relation to each other, and the spacing distance between the feet portion 312 and the rear resection guide surface 211 is obtain by reading the scale of the secondary size-reading portion 313 which is pointed by the secondary size-indicating portion 241. The spacing distance between the feet portion 312 and the rear resection guide surface 211 corresponds to a resection amount of the posterior portion P of the femur F when the feet portion 312 is allocated as leaning against the posterior condyle C2 of the femur F. However, the present invention is not limited to this. Referring to FIG. 6B, according to another embodiment of the present invention, the secondary scale marked portion is provided on the connecting base 24 and the rear scale member 22. Specifically, the secondary size-indicating portion 241a is provided on the connecting base 24, and the secondary size-reading portion 313a is provided on the rear scale member 22.

Preferably, referring to FIG. 4, the rear scale member 22 and the rotatable circular base 32 is integral to provide an external rotation scale marking portion for displaying the rotation angle of the feet portion 312. Specifically, the external rotation scale marked portion includes an external rotation-indicating portion 222 provided on the rear scale member 22 and an external rotation-reading portion 321 provided on the rotatable circular base 32. When the feet portion 312 is being rotated, a eccentric rotor 33 is rotating along with the rotation of the longitudinal portion 311 in the rotatable circular base 32 by being deviated from a rotation axis of the rotatable circular base 32, so as to enable the external rotation-reading portion 321 to display the rotation angle of the feet portion 312 on the external rotation-indicating portion 222.

The locking means 4 includes a first locking member 41 and a second locking member 42. The first locking member 41 is provided between the front scale member 12 and the rear scale member 22 for locking them in a locked state. The second locking member 42 is provided between the rear scale member 22 and the reference gauge means 3 for locking them in a locked state. As an alternative, the locking means 4 may only include either the first locking member 41 or the second locking member 42.

Preferably, each front scale member 12 is extended outwardly to form a wing portion 123. The wing portions 123 are provided with two positioning holes H respectively for positioning a cutting block (not shown). Alternatively, the wing portions 123 having the wing portions 123 may be formed by extending from the rear scale member 22.

Figure 7:
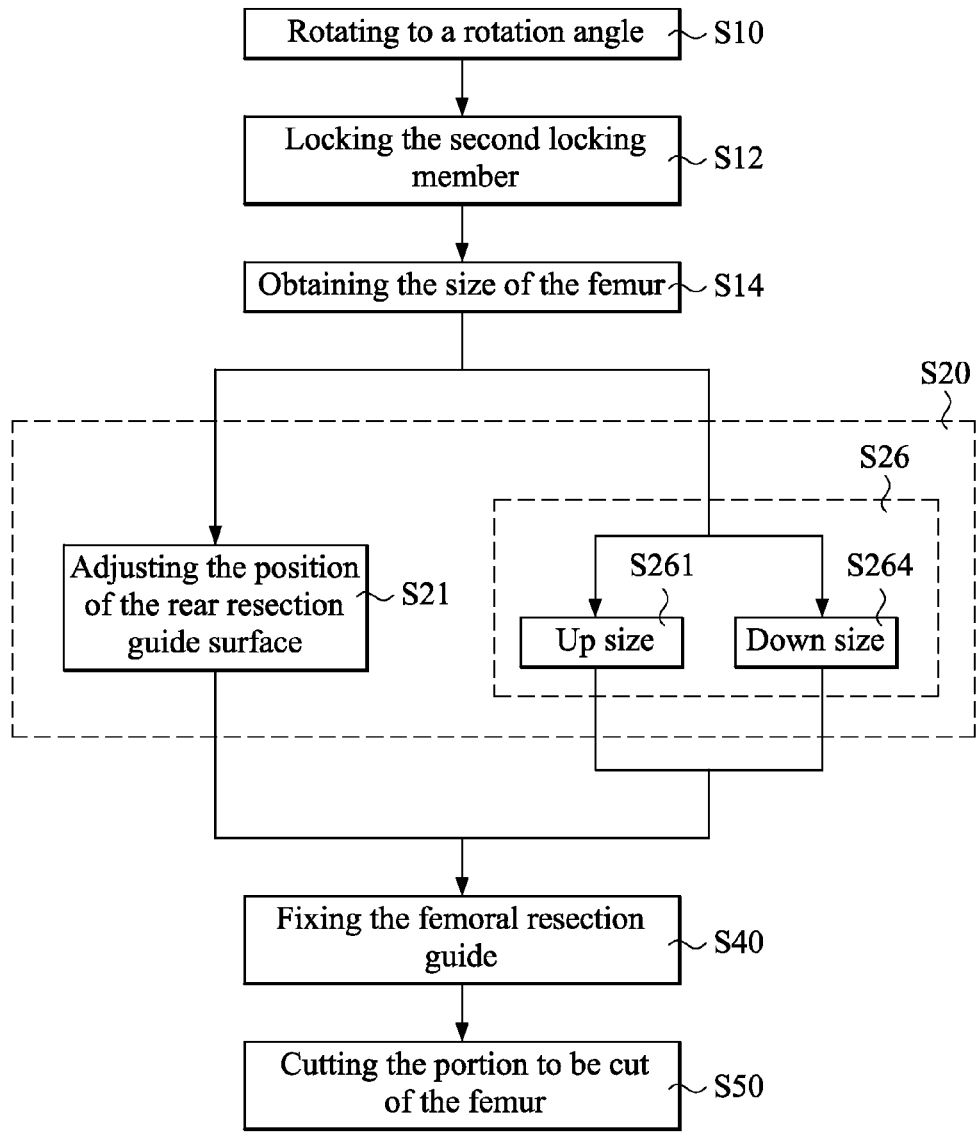
FIG. 7 is a flowchart of a method for using the femoral resection guide to measure and to cut the femur according to an embodiment of the present invention.

Referring to FIG. 7, a method that uses the femoral resection guide 100 for cutting the femur F at the anterior portion A and the posterior portion P comprises steps of: first, obtaining the size of the femur F by positioning the femoral resection guide 100 on the distal section D of the femur F, and sliding the front block 1 and the rear block 2 relative to each other to lean the feet portion 312 of the reference gauge means 3 against a posterior condyle C2 of the femur F and make the stylus 111 be in contact with the anterior cortex C1 of the femur F (step 14). Then, adjusting a spacing distance between the front resection guide surface 112 of the front block 1 and the rear resection guide surface 211 of the rear block 2, the spacing distance being corresponding to a size of an implant which is adapted to the femur F (step 20). After that, directing the front resection guide surface 112 and the rear resection guide surface 211 to a position corresponding to a portion to be cut on the distal section D of the femur F by adjusting the longitudinal portion 311 of the reference gauge means 3 in a direction along the length adjustment direction D2 to a selected adjustably fixed portion and shifting the front block 1 and the rear block 2 relative to the reference gauge means 3 (step 30). Afterwards, fixing the front block 1 and the rear block 2 on the distal section D of the femur F by passing a fixed nail N through the fixed hole (step 40). Finally, cutting the portion to be cut of the femur F by taking the front resection guide surface 112 of the front block 1 and/or the rear resection guide surface 211 of the rear block 2 as a reference resection plane (step 50).

All steps in this method will be described in detail below. It will be appreciated that the specification may have presented the method of the present invention with a particular sequence of steps. However, the method does not rely on the particular sequence of steps set forth herein, and under reasonable circumstances, other sequences of steps may be possible. Therefore, the particular sequence of the steps set forth in the specification should not be construed as limitations on the claims.

Referring to FIG. 7 in conjunction with FIG. 4, selectively, the front block 1 and the rear block 2 are being rotated until to a rotation angle relative to the feet portion 312 of the reference gauge means 3 according to an external rotation angle of the femur (step 10), and the rear block 2 and the reference gauge means 3 are locked by the second locking member 42 (step 12). In the embodiment, the rotation angle of the front block 1 in relation to the rear block 2 is 5 degrees. Selectively, a method for using the femoral resection guide 100a further includes, before the step 12, a step of fixing the reference gauge means 3 on the distal section D of the femur F by passing a fixed nail N through the fixed hole 314 of the reference gauge means 3.

Figure 8A:
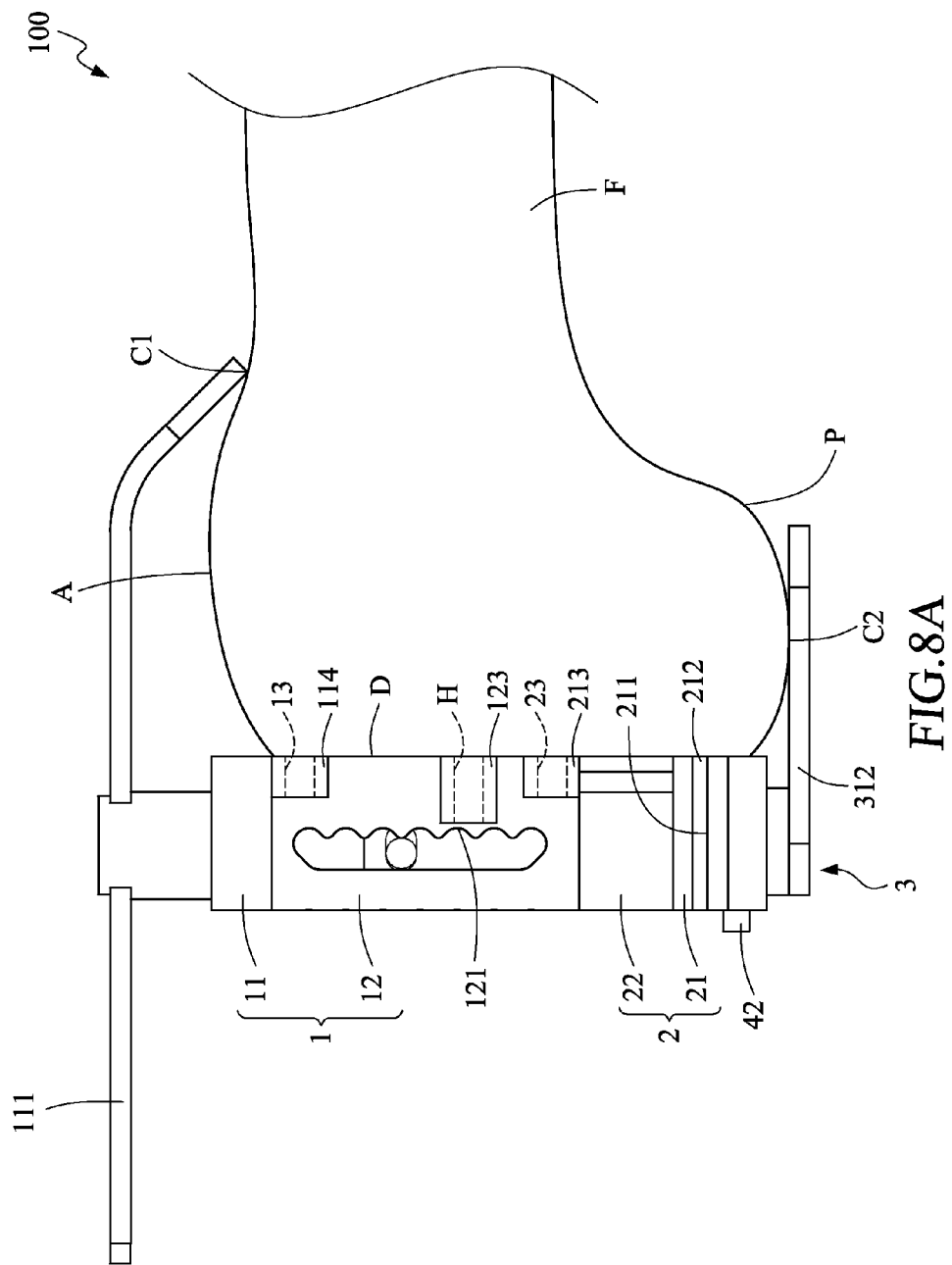
FIGS. 8A, 8B, 10 to 13, 15, 17 and 18 are schematic views illustrating the processes of the method of the present invention.
Figure 8B:
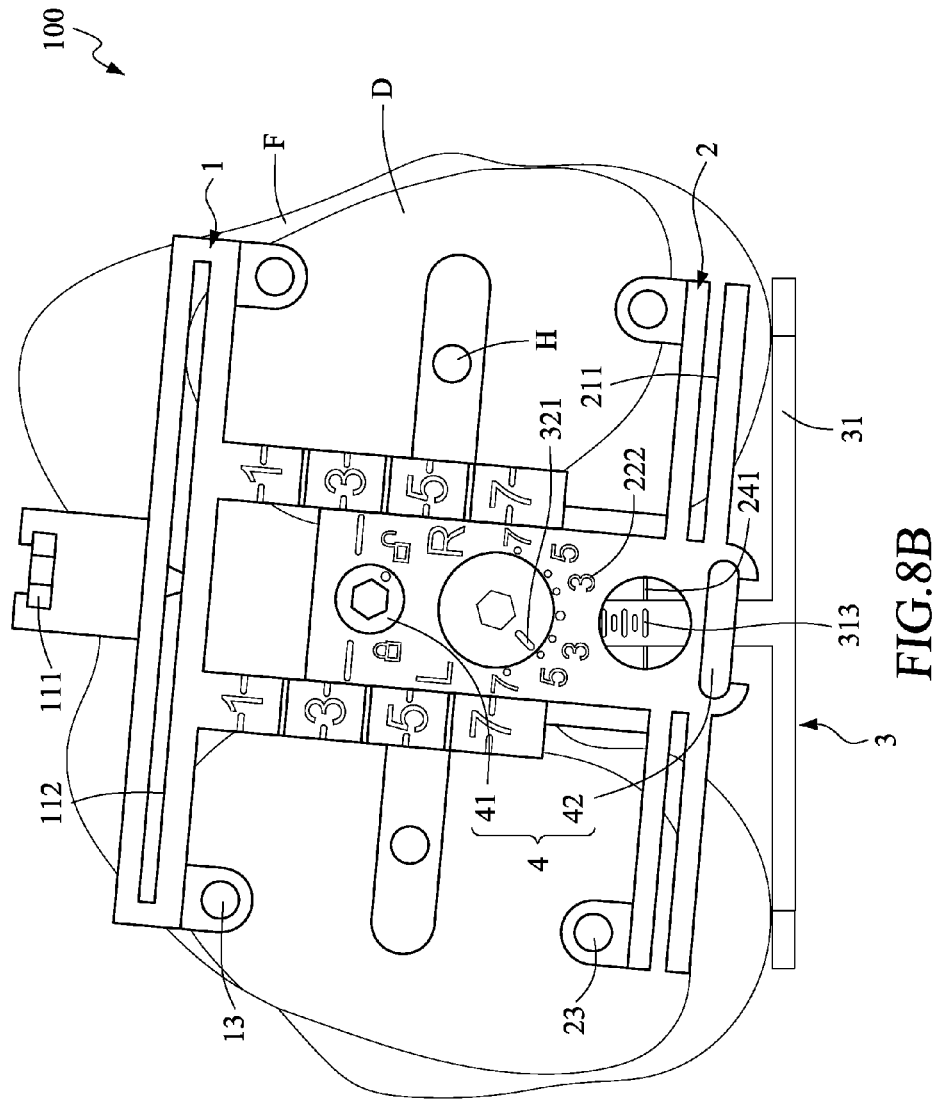

Referring to FIGS. 7, 8A, 8B, the size of the femur F is obtained by reading a scale of main size-indicating portion 122 which is pointed by the rear resection guide surface 211 in a state that the feet portion 312 is leaning against a posterior condyle C2 of the femur F and the stylus 111 is therefore in contact with the anterior cortex C1 of the femur F (step 14). In the present embodiment, the main size-reading portion 221 points at a position of the indicia mark of 3.5 on the main size-indicating portion 122. A surgeon can either choose a scale mark of 3 (i.e. downward size) or a scale mark of 4 (i.e. upward size) by sliding the front block 1 and the rear block 2 in relation to each other, so as to select an implant corresponding to the scale a mark of 3 or an implant corresponding to the scale mark of 4.

Referring to FIG. 7, in the step 20, the portion to be cut of the femur F is cut by taking the rear resection guide surface 211 of the rear block 2 as a reference resection plane (step 21) or cutting the portion to be cut of the femur F by taking the front resection guide surface 112 of the front block 1 as a reference resection plane (step 26).

Figure 9:
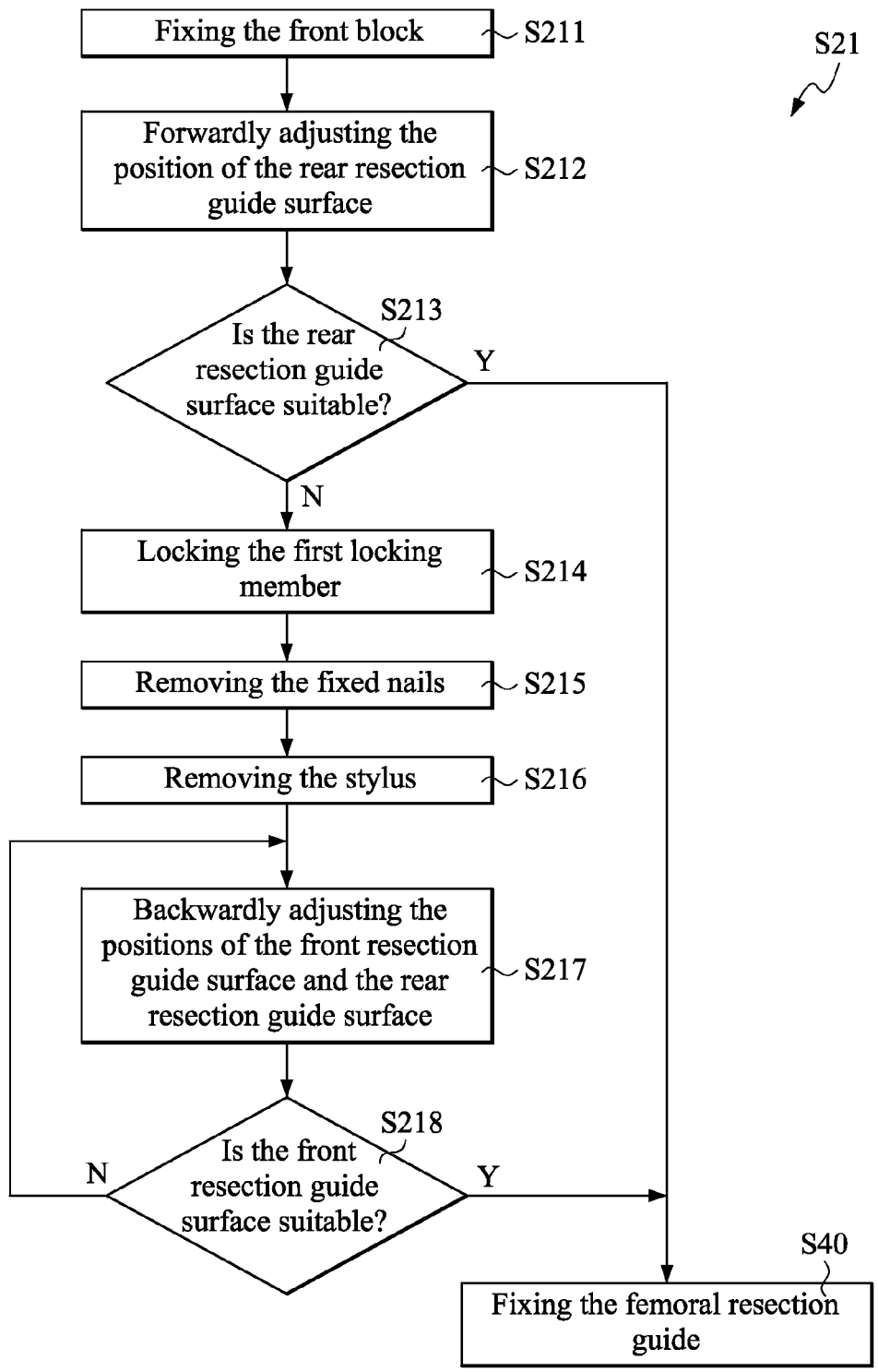
FIG. 9 is a detailed flowchart of a step 21 of the method of the present invention.
Figure 10:
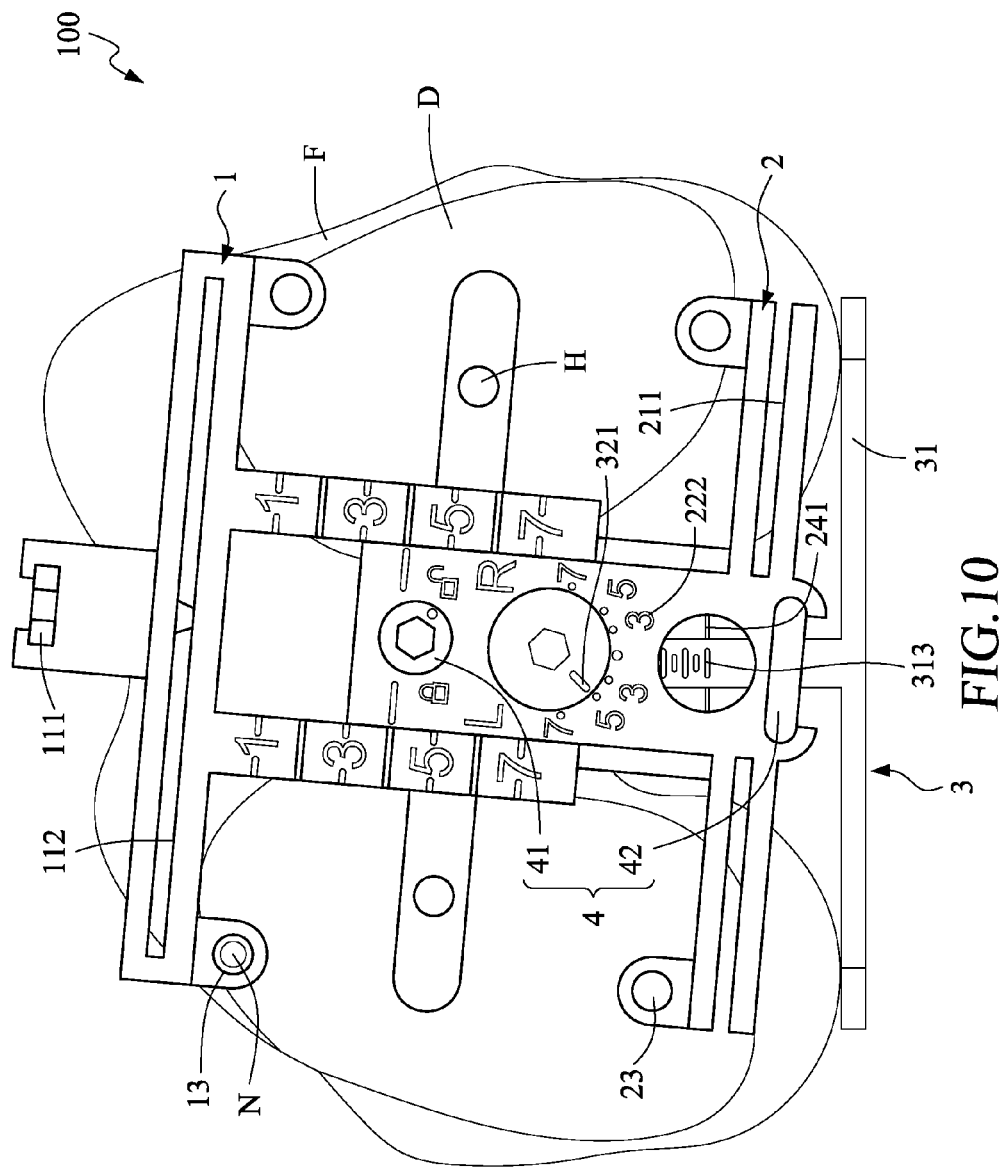
Figure 11:
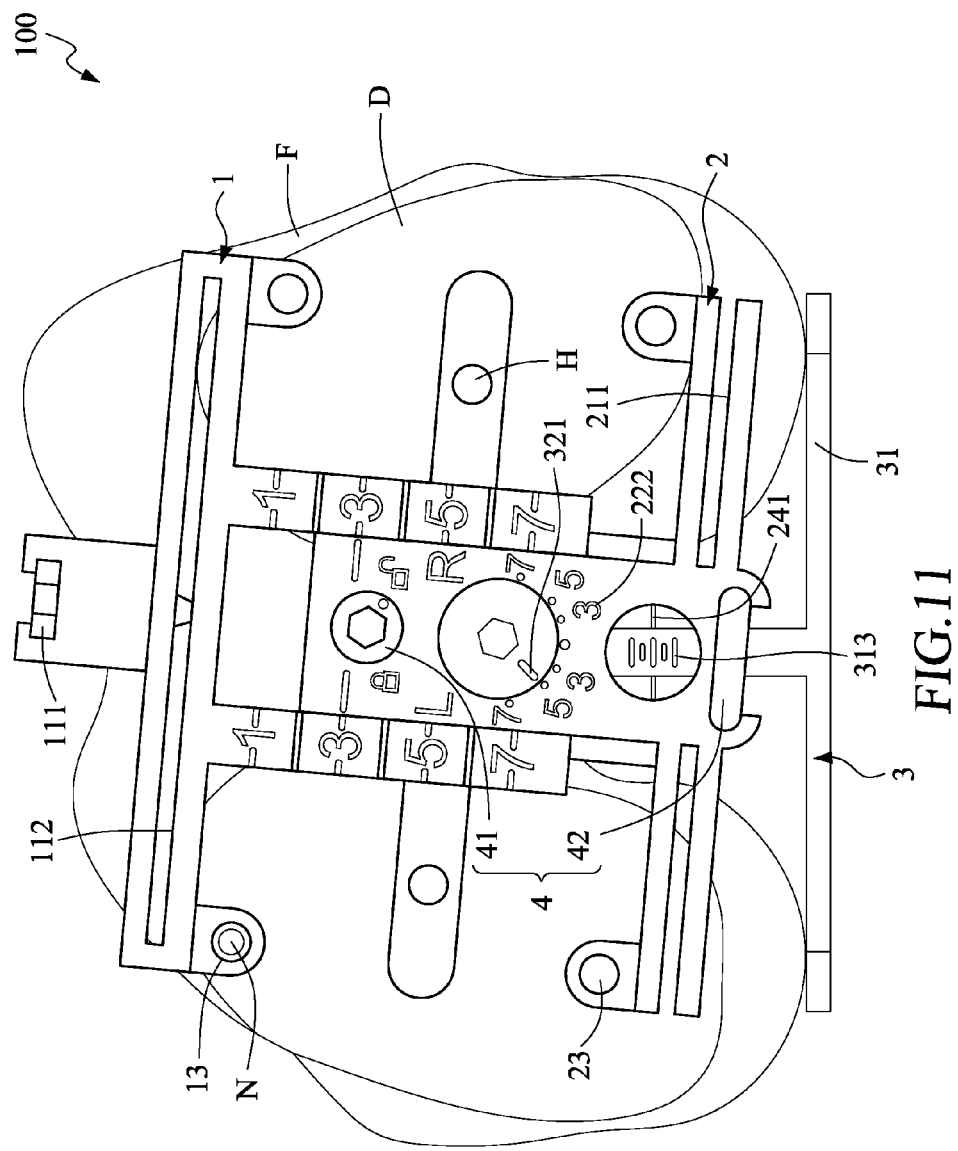

Specifically, referring to FIGS. 9 and 10, in step S21, the front block 1 is fixed on the distal section D of the femur F by passing a fixed nail N through the fixed hole 13 of the front block 1 (step 211). Referring to FIGS. 9 and 11, the position of the rear resection guide surface 211 is forwardly adjusted in a manner that utilizes the main size-reading portion 221 to point to the scale mark of 3 on the main size-indicating portion 122 by sliding the rear block 2 forwardly when the second locking member 42 is unlocked (step 212). It will be appreciated that in the step 212, the reference member 31 is kept leaning against a posterior condyle C2 of the femur F, and the spacing distance between the feet portion 312 and the rear resection guide surface 211 is increased when the rear block 2 is sliding forwardly. After the position of the rear resection guide surface 211 is adjusted, the second locking member 42 returns to the locked state. The position of the rear resection guide surface 211 is determined as being suitable or not (step 213).

Figure 12:
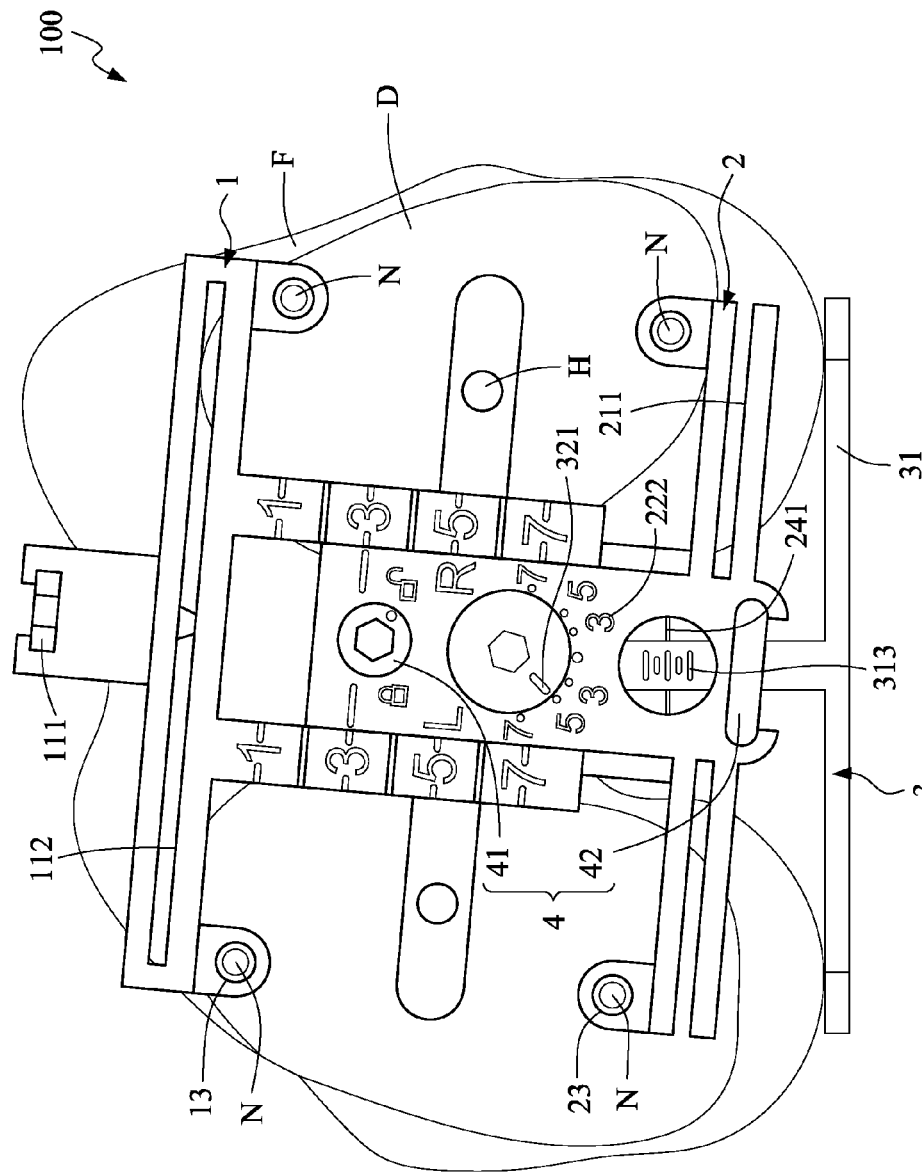

In case that the position of the rear resection guide surface 211 is suitable, referring to FIGS. 9 and 12, the femoral resection guide 100 is fixed on the distal section of the femur F by passing plurality of fixed nails through the fixed hole 13, the fixed hole 23 and the positioning hole H (step 40). Thereafter, the anterior portion A of the femur F is cut along the front resection guide surface 112 of the front block 1 and the posterior portion P of the femur F along the rear resection guide surface 211 of the rear block 2 by the cutting tool (step 50).

Figure 13:
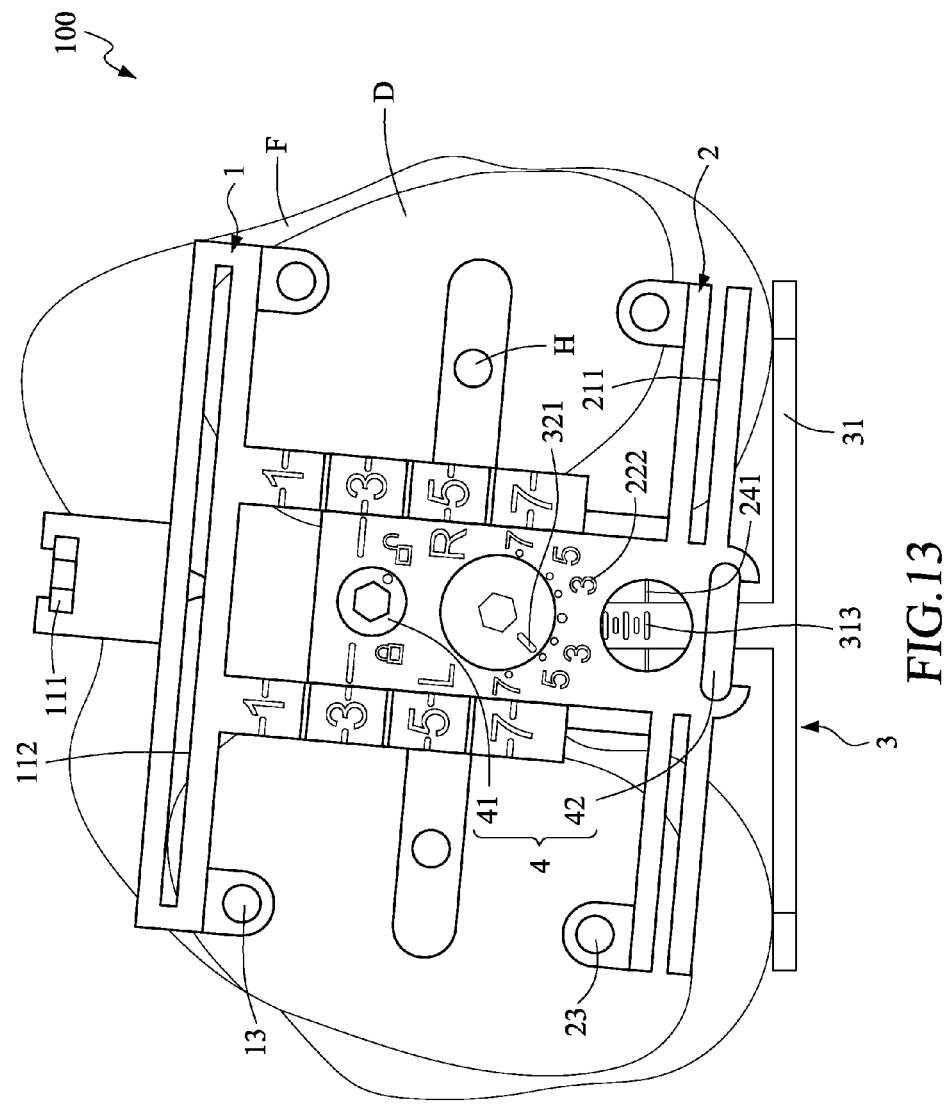

Referring to FIG. 9, in case that the position of the rear resection guide surface 211 is not suitable, the front block 1 and the rear block 2 are locked by the first locking member 41 (step 214). Referring to FIGS. 9 and 13, the fixed nails passed on the fixed hole 13 of the front block 1 (step 215) and the stylus 111 is removed (step 216). Referring to FIGS. 9 and 13, the positions of the front resection guide surface 112 of the front block 1 and the rear resection guide surface 211 of the rear block 2 are backwardly adjusted in such a manner that the spacing distance between the feet portion 312 and the rear resection guide surface 211 is reduced by backwardly sliding the front block 1 and the rear block 2 in relation to the reference member 31 (step 217). The position of the front resection guide surface 112 is determined as being suitable or not (step 218). The step 40 is executed when the position of the front resection guide surface 112 is suitable. The step 207 is repeatedly executed until the position of the front resection guide surface 112 becomes suitable if the front resection guide surface 112 is not being suitable.

Referring to FIG. 6, in the step 26, either the scale mark of 4, i.e. upward size, (step 261) or the scale mark of 3, i.e. downward size (step 264), on the main size-indicating portion 122 pointed by the main size-reading portion 221 can be chosen.

Figure 14:
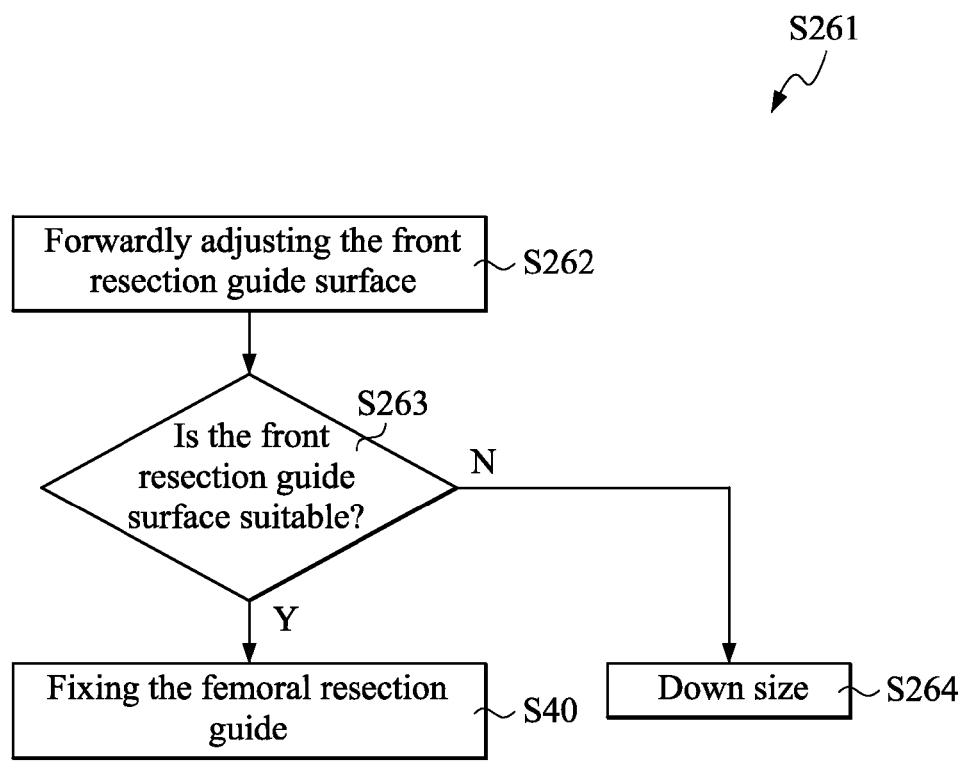
FIG. 14 is a detailed flowchart of a step 261 of the method of the present invention.
Figure 15:
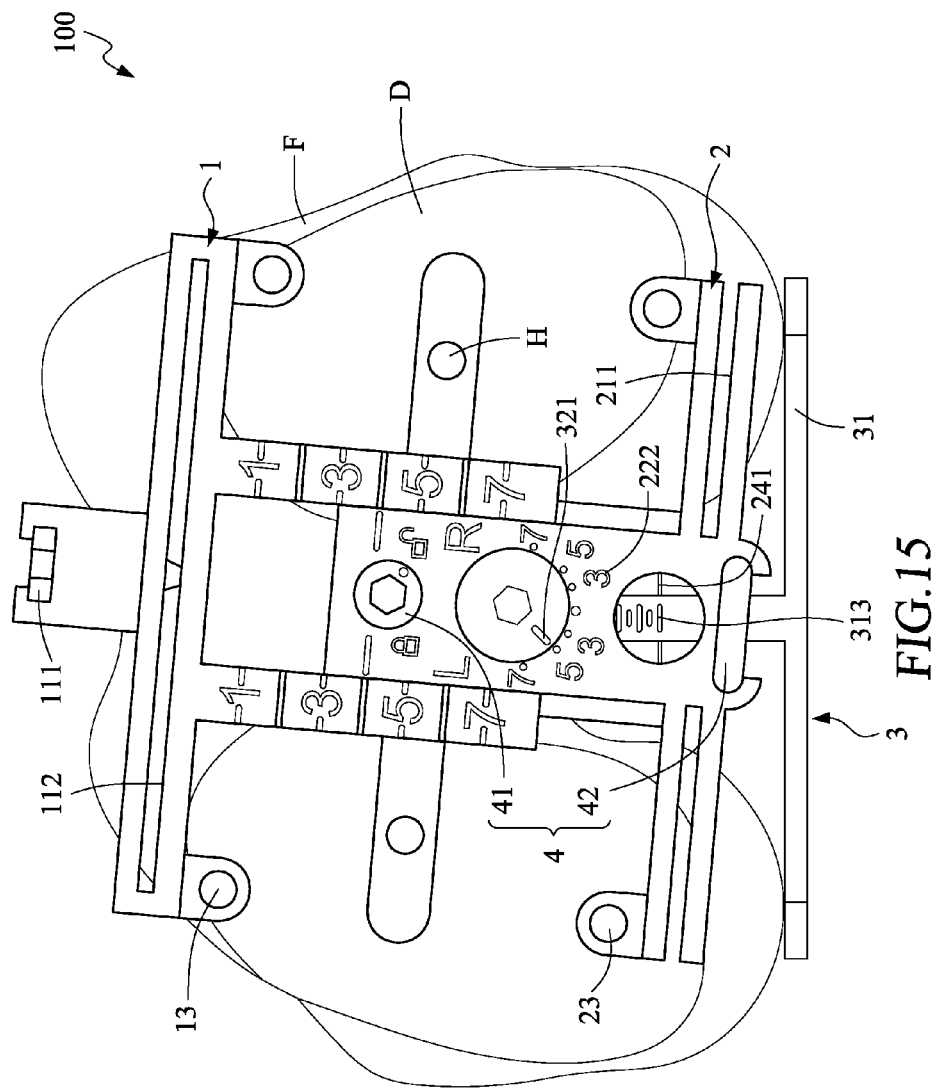

The step 261 includes the steps of: referring to the FIGS. 14 and 15, enabling the main size-reading portion 221 to point to the position of the indicia mark of 4 on the main size-indicating portion 122 by forwardly sliding the front block 1 in relation to the rear block 2 and the feet portion 312 to forwardly adjust the position of the front resection guide surface 112 (step 262). Then, determining the position of the front resection guide surface 112 is being suitable or not (step 263). Executing the step 40 when the position of the front resection guide surface 112 is suitable. Repeatedly executing the step 264 when the front resection guide surface 112 is unsuitable.

Figure 16:
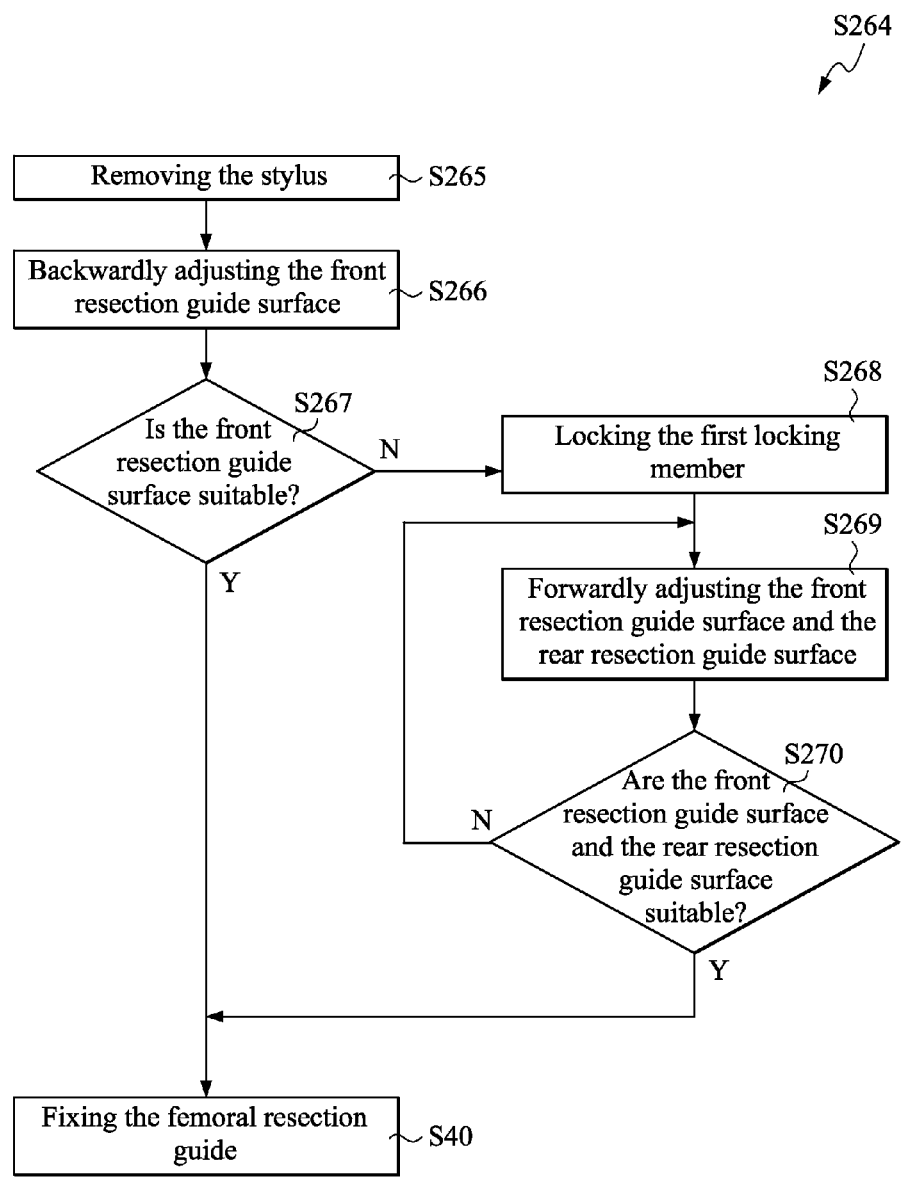
FIG. 16 is a flowchart detailing a step 264 of the method.
Figure 17:
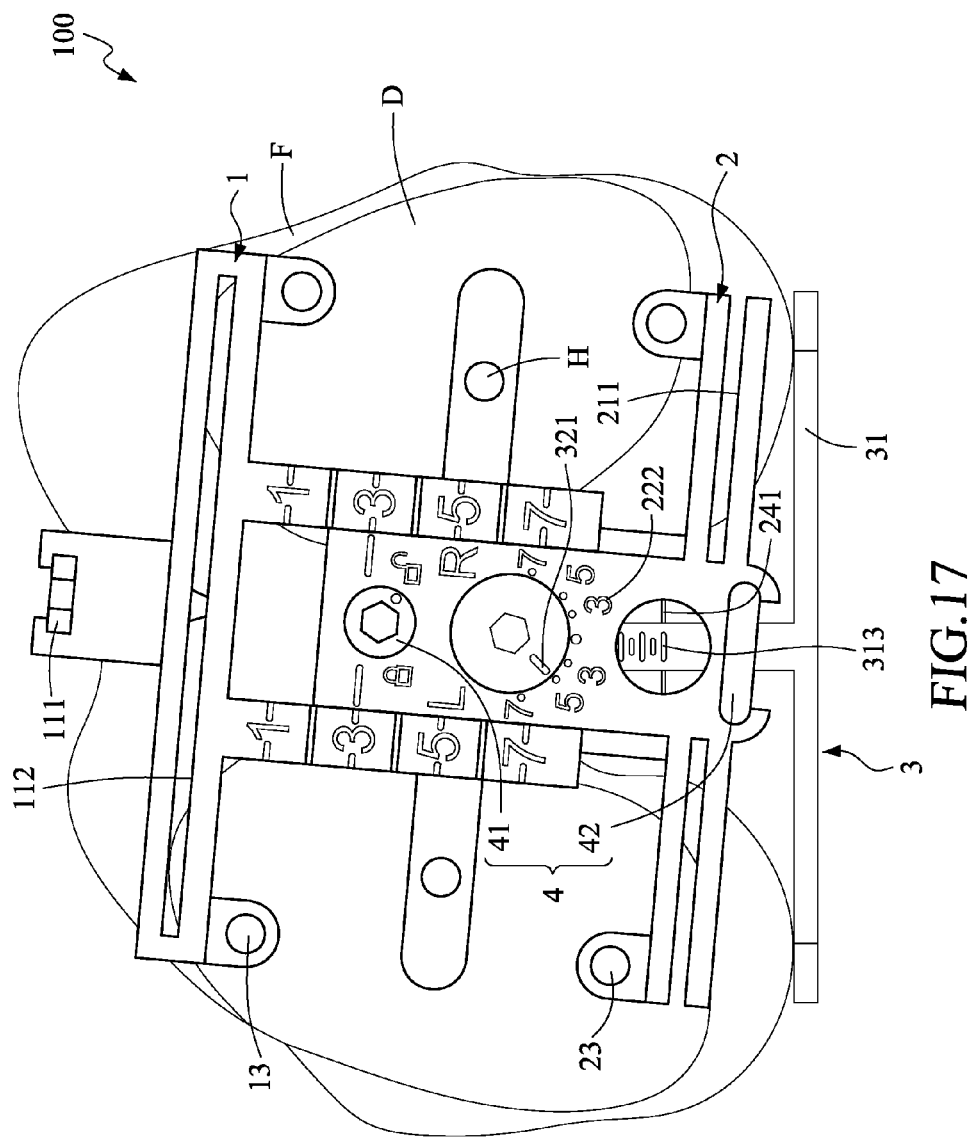
Figure 18:
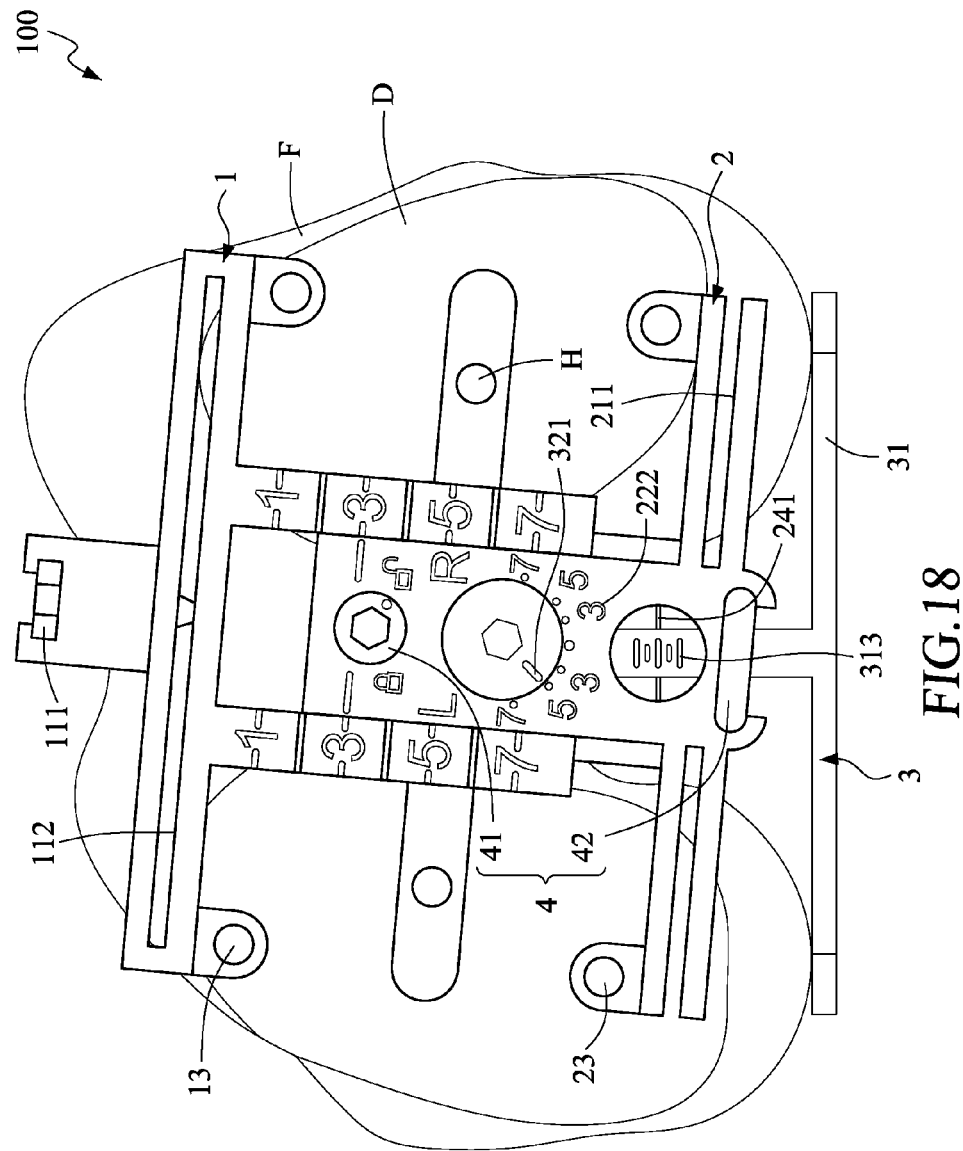

The step 264 includes the steps of: referring to the FIGS. 16 and 17, the stylus 111 is removed (step 265), and the main size-reading portion 221 is enabled to point at the position of the indicia mark of 3 on the main size-indicating portion 122 by backwardly sliding the front block 1 relative to the rear block 2 and the feet portion 312 to backwardly adjust the position of the front resection guide surface 112 (step 266). Determining the position of the front resection guide surface 112 is being suitable or not (step 267). Executing the step 40 when the position of the front resection guide surface 112 is suitable.

Referring to the FIG. 16, the front scale member 12 and the rear scale member 22 is locked by the first locking member 41 when the front resection guide surface 112 is unsuitable (step 268). Referring to the FIG. 18, the positions of the front resection guide surface 112 of the front block 1 and the rear resection guide surface 211 of the rear block 2 is forwardly adjusted in a manner that forwardly adjusting the front block 1 and the rear block 2 to increase the spacing distance between the feet portion 312 and the rear resection guide surface 211 (step 269). Then, determining the positions of the front resection guide surface 112 and the rear resection guide surface 211 are being suitable are not (step 270).

It is noted that, according to this embodiment, the step of adjusting the spacing distance between the front resection guide surface 112 and the rear resection guide surface 211 by sliding the front block 1 and the rear block 2 relative to each other is performed firstly, and then the step of adjusting the position of the femoral resection guide 100 which is positioned on the femur F and adjusting the resection amount of the posterior portion P of the femur F by adjusting the reference member 31 is secondly performed. Selectively, the step of adjusting the position of the femoral resection guide 100 which is positioned on the femur F and adjusting the resection amount of the posterior portion P of the femur F by adjusting the reference member 31 can be executed firstly, and then the step of adjusting the spacing distance between the front resection guide surface 112 and the rear resection guide surface 211 by sliding the front block 1 and the rear block 2 in relation to each other can be then secondly executed.

The above describes the preferred embodiments of the present invention. The above description is not intended to limit the scope of the present invention, so the equivalent structural changes according to the above specification and the accompanied claims of the present invention are considered to be included within the scope of the present invention.

What is claimed is:

1. A femoral resection guide for measuring and guiding resection of an anterior portion and a posterior portion of a femur, comprising:
   a front block provided with a front datum member and a front scale member, wherein the front datum member is provided with a stylus for contacting an anterior cortex of the femur and has a front resection guide surface for guiding a cutting tool to resect the anterior portion of the femur, the front scale member is provided extending backwardly from the front datum member along an extending direction and is formed with a plurality of adjustably fixed portions arranged along the extending direction, and the front block has a front fixed hole by which the front block is enabled to fix on a distal section of the femur;
   a rear block provided with a rear datum member and a rear scale member, wherein the rear datum member is provided with a rear resection guide surface for guiding a cutting tool to cut the posterior portion of the femur, the rear scale member includes a connecting base and is provided extending forwardly from the rear datum member along the extending direction and is slidingly engaged with the front scale member, and the rear block has a rear fixed hole by which the rear block is enabled to fix on the distal section of the femur;
   a reference gauge means provided with a reference member, wherein the reference member is provided with a longitudinal portion extended along a length adjustment direction and a feet portion connected with the longitudinal portion, the longitudinal portion is provided on the rear block and is slidingly socketed in the connecting base in an adjustment position along the length adjustment direction, the feet portion and the rear resection guide surface are provided therebetween with a spacing distance corresponding to a resection amount of the posterior portion of the femur, the feet portion is used to contact the posterior condyle of the femur; and
   a locking means provided between the front scale member and the rear scale member for locking them in a locked state or provided between the rear scale member and the reference gauge means for locking them in a locked state,
   wherein a main scale marked portion is provided corresponding to both the front scale member and the rear scale member, and a measurement is performed by sliding the rear scale member and the front scale member relative to each other along the extending direction to an adjusted position defined by a selected one of the adjustably fixed portions.

2. The femoral resection guide as claimed in claim 1, wherein the front datum member is provided with a front guiding slot having the front resection guide surface.

3. The femoral resection guide as claimed in claim 1, wherein the rear datum member is provided with a rear guiding slot having the rear resection guide surface.

4. The femoral resection guide as claimed in claim 1, wherein a wing portion is formed extending from the front block or the rear block, and the wing portion has a positioning hole to allow a femoral cutting block to be installed.

5. The femoral resection guide as claimed in claim 1, wherein the stylus is provided removable from the front datum member.

6. The femoral resection guide as claimed in claim 1, wherein a secondary scale marked portion is provided corresponding to the connecting base and the longitudinal portion to display the spacing distance between the feet portion and the rear resection guide surface.

7. The femoral resection guide as claimed in claim 1, wherein a secondary scale marked portion is provided corresponding to the connecting base and the rear scale member to display the spacing distance between the feet portion and the rear resection guide surface.

8. The femoral resection guide as claimed in claim 1, wherein the connecting base is pivotally disposed on the rear scale member in such a manner that the feet portion pivots on the connecting base, the reference gauge means includes a rotatable circular base and an eccentric rotor, the rotatable circular base is disposed on the rear scale member, the eccentric rotor is disposed on the rotatable circular base by being deviated from a rotation axis of the rotatable circular base, and the longitudinal portion is slidingly connected with the eccentric rotor.

9. The femoral resection guide as claimed in claim 8, wherein an external rotation scale marked portion is provided corresponding to the rear block and the rotatable circular base to display the rotation angle of the feet portion.

10. The femoral resection guide as claimed in claim 1, wherein the reference member has a fixed hole by which the reference member is enabled to fix on the distal section of the femur.

* * * * *